United States Patent
Liberatore et al.

(10) Patent No.: US 7,452,368 B2
(45) Date of Patent: Nov. 18, 2008

(54) SYSTEM FOR HOLDING SURGICAL FASTENERS

(75) Inventors: Jessica Liberatore, Marlboro, NJ (US); Mark Howansky, Union City, NJ (US); Gene W. Kammerer, East Brunswick, NJ (US); James J. Rudnick, Mahwah, NJ (US)

(73) Assignee: Ethicon, Inc., Somerville, NJ (US)

( * ) Notice: Subject to any disclaimer, the term of this patent is extended or adjusted under 35 U.S.C. 154(b) by 862 days.

(21) Appl. No.: 10/941,238

(22) Filed: Sep. 15, 2004

(65) Prior Publication Data

US 2006/0058818 A1    Mar. 16, 2006

(51) Int. Cl.
*A61D 1/00* (2006.01)

(52) U.S. Cl. .................. 606/220; 606/143; 206/339

(58) Field of Classification Search .......... 606/139, 606/142, 143, 219, 220, 221; 206/339, 340, 206/341; 24/114.7; 227/67
See application file for complete search history.

(56) References Cited

U.S. PATENT DOCUMENTS

| | | |
|---|---|---|
| 4,006,747 A | 2/1977 | Kronenthal et al. |
| 4,235,238 A | 11/1980 | Ogiu et al. |
| 4,669,474 A | 6/1987 | Barrows |
| 4,705,040 A | 11/1987 | Mueller et al. |
| 5,007,921 A | 4/1991 | Brown |
| 5,085,661 A | 2/1992 | Moss |
| 5,203,864 A | 4/1993 | Phillips |
| 5,279,416 A | 1/1994 | Malec et al. |
| 5,290,296 A | 3/1994 | Phillips |
| 5,290,297 A | 3/1994 | Phillips |
| 5,307,924 A * | 5/1994 | Manosalva et al. ......... 206/63.3 |
| 5,320,633 A | 6/1994 | Allen et al. |
| 5,341,823 A * | 8/1994 | Manosalva et al. .......... 128/898 |
| 5,411,522 A | 5/1995 | Trott |

(Continued)

FOREIGN PATENT DOCUMENTS

EP    0 129 442 A    12/1984

(Continued)

OTHER PUBLICATIONS

U.S. Appl. No. 10/959,787, filed Oct. 6, 2004.

(Continued)

*Primary Examiner*—Kevin T. Truong
*Assistant Examiner*—Eric Blatt

(57) ABSTRACT

A system for holding surgical fasteners each having a first anchor, a second anchor and a connector extending therebetween upwardly from the first and second anchors, and a method for loading the same into an applicator. The system includes a shuttle having first and second channels dimensioned to slidably receive therein the first and second anchors, and having first and second grooves respectively forming openings into the channels along a portion of a length of the channels. When the first and second anchors are received within the first and second channels, the connector of the surgical fastener extends out of the shuttle through the first and second grooves. The system also includes a cartridge having at least a first channel dimensioned to slidably receive the shuttle therein, and having a first projection extending into the first channel. When the shuttle and loaded fastener are received within the cartridge channel, the connector of the surgical fastener abuts the first projection to thereby limit movement of the fastener toward a distal end of the cartridge.

20 Claims, 13 Drawing Sheets

U.S. PATENT DOCUMENTS

| | | |
|---|---|---|
| 5,470,337 A | 11/1995 | Moss |
| 5,474,557 A | 12/1995 | Mai |
| 5,603,404 A | 2/1997 | Nazare et al. |
| 5,941,439 A | 8/1999 | Kammerer et al. |
| 6,152,935 A | 11/2000 | Kammerer et al. |
| 6,156,044 A | 12/2000 | Kammerer et al. |
| 6,623,492 B1 | 9/2003 | Berube et al. |
| 2002/0077660 A1 | 6/2002 | Kayan et al. |
| 2003/0045889 A1 | 3/2003 | Kayan et al. |
| 2003/0135226 A1 | 7/2003 | Bolduc et al. |
| 2004/0040875 A1 | 3/2004 | Gallagher |
| 2005/0288689 A1* | 12/2005 | Kammerer et al. .......... 606/142 |
| 2007/0060929 A1* | 3/2007 | Onishi et al. ................ 606/139 |

FOREIGN PATENT DOCUMENTS

| | | |
|---|---|---|
| EP | 0 847 727 B1 | 2/2004 |
| WO | WO 87/01270 A1 | 3/1987 |
| WO | WO 98/51179 A1 | 11/1998 |
| WO | WO 02/04318 A | 1/2002 |

OTHER PUBLICATIONS

U.S. Appl. No. 10/876,991, filed Jun. 25, 2004 (now abandoned).
U.S. Appl. No. 10/877,669, filed Jun. 25, 2004.

* cited by examiner

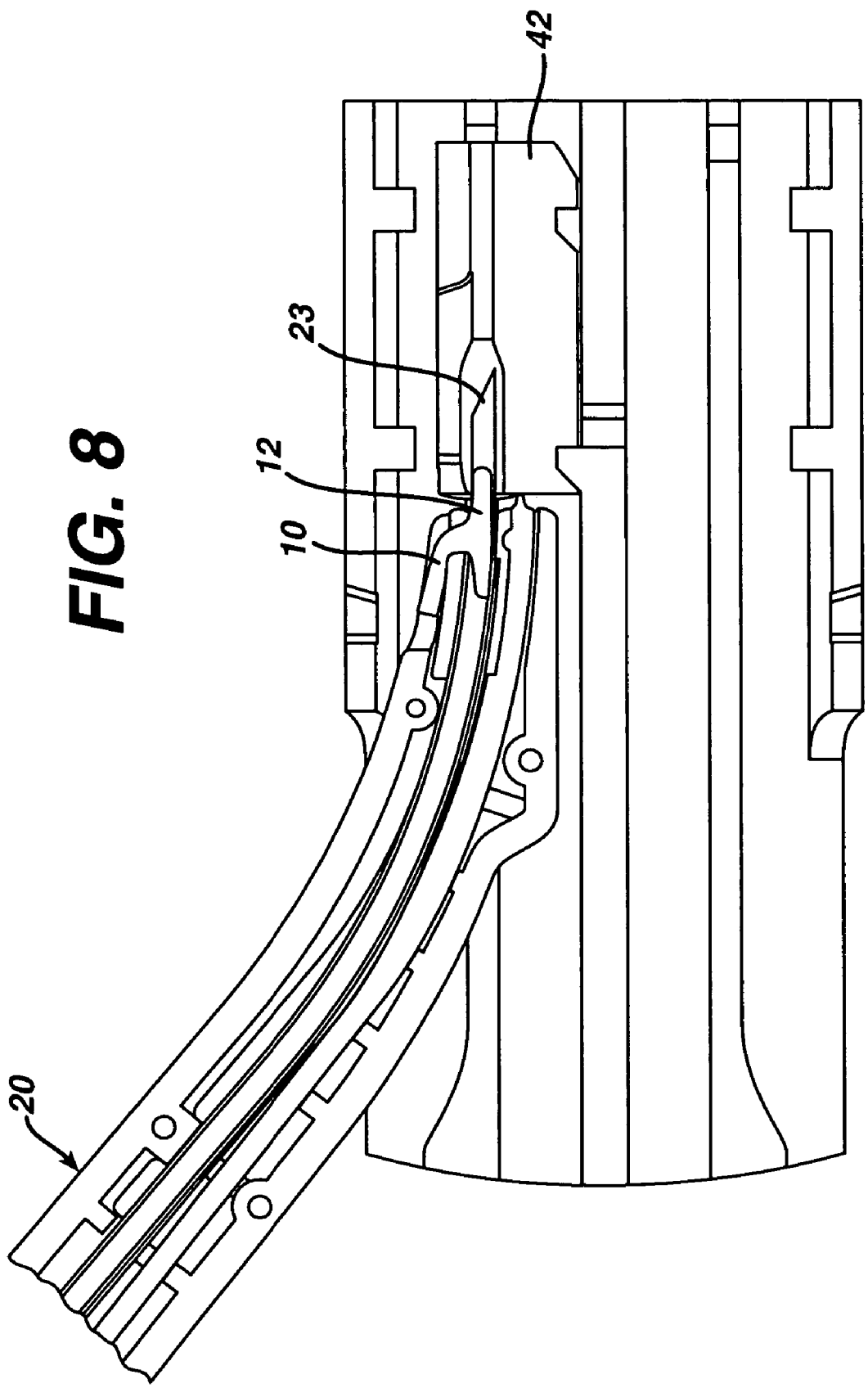

SYSTEM FOR HOLDING SURGICAL FASTENERS

FIELD OF THE INVENTION

The present invention relates generally to a system for holding surgical fasteners, and more particularly to a system that facilitates loading of the surgical fasteners into a surgical applicator.

BACKGROUND OF THE INVENTION

Surgical fasteners are frequently used in a variety of surgical procedures in which different portions of tissue, ligaments or the like must be brought together and held in place. For example, surgical fasteners have been used to repair cartilage or ligament tears, such as with shoulder or knee injuries. Surgical fasters may also be used to approximate tissue, such as during various pelvic floor repair procedures. They also provide a convenient and efficient way to secure various prosthetic devices to tissue, such as meshes used for hernia repair.

Surgical fasteners are typically deployed using a surgical "gun" or applicator that is designed to embed the given fastener in the proper place within the body. These surgical applicators typically include one or more sharp or penetrating element that is inserted into the tissue to be approximated, ligament, or the like, and a deployment mechanism that will subsequently drive the fastener out of the applicator and embed it into the tissue through the passageway made by the penetrating element(s).

One such surgical fastener and applicator are described in detail in co-pending U.S. patent application Ser. Nos. 10/876,991 and 10/877,669, which were filed on Jun. 25, 2004, and which are incorporated herein by reference in their entirety. FIGS. 1 and 2 illustrate this fastener and surgical applicator, and FIGS. 7 and 8 illustrate the fastener being loaded into the gun. As shown in FIG. 1, the surgical fastener 10 includes first and second anchors 12, 14 and a connector portion 16 extending therebetween. At least first and second connector segments 18a, 18b of the fastener are resiliently biased so that when the surgical fastener is straightened by an external force (such as occurs during application of the fastener with the applicator), it is biased to return to the configuration shown in FIG. 1. The fastener is otherwise somewhat flexible, as it is preferably made of polypropylene of other similar plastic material. FIG. 2 illustrates a surgical applicator that can be used to deploy the fastener of FIG. 1. The applicator 20 includes first and second needles 21, 22 having a pointed or tissue penetrating distal end and having channels 23, 24 therein.

Referring now to FIG. 8, to load the surgical fastener 10 into applicator 20, the first and second anchors 12, 14 must be inserted into the first and second channels 23, 24 of the first and second needles 21, 22. This is a difficult task, however, because the surgical fastener is flexible and difficult to hold steady during loading. Further, much care must be exercised when loading the anchors into the channels to avoid being cut by the sharp distal ends of the needles. For one known H-type flexible fastener, the mechanism developed for loading the fasteners into an applicator involved preloading the fastener into a needle for the applicator, and separately packaging this needle/fastener combination. The preloaded needles are then inserted into the applicator to thereby load the applicator. This type of system and applicator, as described more fully in U.S. Pat. Nos. 5,984,097 and 6,047,826, does not address safety concerns relating to loading the fasteners directly into the sharp needles, and requires a new needle for every fastener. Thus, it would be desirable to provide an improved, reliable, simpler and safer mechanism for loading surgical fasteners into a surgical applicator.

SUMMARY

The present invention provides a system for holding one or more surgical fasteners each having a first anchor, a second anchor and a connector extending therebetween upwardly from the first and second anchors, wherein the system includes a shuttle having first and second channels dimensioned to slidably receive therein the first and second anchors, and having first and second grooves respectively forming openings into the channels along a portion of a length of the channels. When the first and second anchors are received within the first and second channels, the connector of the surgical fastener extends out of the shuttle through the first and second grooves. The system further includes a cartridge having at least a first channel dimensioned to slidably receive the shuttle therein, and having a first projection extending into the first channel. When the shuttle and loaded fastener are received within the cartridge channel, the connector of the surgical fastener abuts the first projection to thereby limit movement of the fastener toward a distal end of the cartridge.

In one embodiment, the cartridge further includes a second projection extending into the cartridge channel that engages a first recess in the shuttle to prevent further movement of the shuttle toward the distal end of the cartridge absent application of a predetermined amount of force against the shuttle. In yet another embodiment, the second projection is a tab element having an inclined edge and movably mounted to the cartridge. Application of the predetermined force to the shuttle causes the second projection to move relative to the cartridge to enable the shuttle to move past the second projection. In yet another embodiment, the cartridge further includes a third projection extending into the cartridge channel. The third projection prevents further movement of the shuttle towards the distal end of the cartridge after the shuttle has moved distal of the second projection.

In another embodiment, the application of the predetermined force to said shuttle enables the shuttle to move past the second projection toward the distal end of the cartridge, but the first projection still prevents movement of the fastener, thereby causing the first and second fastener anchors to be ejected from the first and second shuttle channels.

The cartridge channel may further be dimensioned to receive therein a distal end of an applicator having first and second hollow needles projecting outwardly therefrom that align with the first and second shuttle channels so that as the first and second anchors are ejected from the first and second shuttle channels, they are received within the hollow needles.

The cartridge channel may also be open to an exterior of the cartridge along a portion of the cartridge channel, and the cartridge may further include a plurality of channels for removably receiving a plurality of shuttles. In yet another embodiment, the proximal end of the first and second shuttle channels are flared. The cartridge may also further include first and second recesses adjacent first and second sides of the cartridge channel respectively, and the shuttle further include first and second side extensions dimensioned to be received within the first and second recesses when the shuttle is inserted into the cartridge channel. The proximal end of the first and second recesses may also be flared.

The system may further include a cartridge holder having a base side and a top side. The top side has a recess therein dimensioned to receive the distal end of the cartridge to thereby hold the cartridge in position relative to a surface on which the cartridge holder is placed. Finally, the cartridge holder may further include a shield element extending outwardly from the cartridge holder toward the top side of the cartridge holder, and extending around at least a portion of a periphery of the cartridge holder.

Also provided is a surgical fastener holding system including a surgical fastener having first and second anchors and a connector extending therebetween upwardly from the first and second anchors, and a shuttle having first and second channels dimensioned to slidably receive therein the first and second anchors of the surgical fastener. The shuttle further has first and second grooves forming openings into the first and second channels respectively along a portion of a length of the channels, wherein when the first and second anchors are received within the first and second channels, the connector of the surgical fastener extends out of the shuttle through the first and second grooves. The system further includes a cartridge having a proximal end, a distal end, and a channel therein extending inwardly from the proximal end. The cartridge channel is dimensioned to slidably receive therein the shuttle, and has first and second projections extending into the channel. When the shuttle and loaded fastener are slidably received in the cartridge channel, the connector of the surgical fastener abuts the first projection to thereby limit further movement of the surgical fastener toward the distal end of the cartridge, and a recess in the shuttle engages the second projection to prevent further movement of the shuttle toward the distal end of the cartridge absent application of a predetermined amount of force against the shuttle.

Finally, a method is provided for loading a surgical fastener into an applicator. The method includes the steps of providing a surgical fastener having a first anchor, a second anchor and a connector extending therebetween upwardly from the first and second anchors, providing a shuttle having first and second channels therein, and first and second grooves respectively forming openings into the channels along a portion of a length of said channels, and inserting the first and second anchors of the surgical fastener into the first and second shuttle channels such that the connector of the surgical fastener extends out of the shuttle through the first and second grooves. The method further includes providing a cartridge having at least a first channel therein and a first projection extending into the first channel, inserting the shuttle and inserted fastener into the cartridge first channel such that the connector of the surgical fastener abuts the first projection to thereby limit further movement of the fastener toward a distal end of the cartridge, and inserting an applicator having first and second hollow needles extending from a proximal end thereof into the cartridge channel such that the first and second hollow needles are aligned with the first and second shuttle channels. Finally, the method includes inserting the applicator further into the cartridge channel to push the shuttle further toward a distal end of the cartridge such that the first and second anchors of the surgical fastener are ejected from the first and second shuttle channels into the first and second hollow needles of the applicator.

BRIEF DESCRIPTION OF THE DRAWINGS

FIGS. 7 and 8 are cut-away views illustrating a fastener being loaded from a shuttle into an applicator;

DETAILED DESCRIPTION

Figure 1:
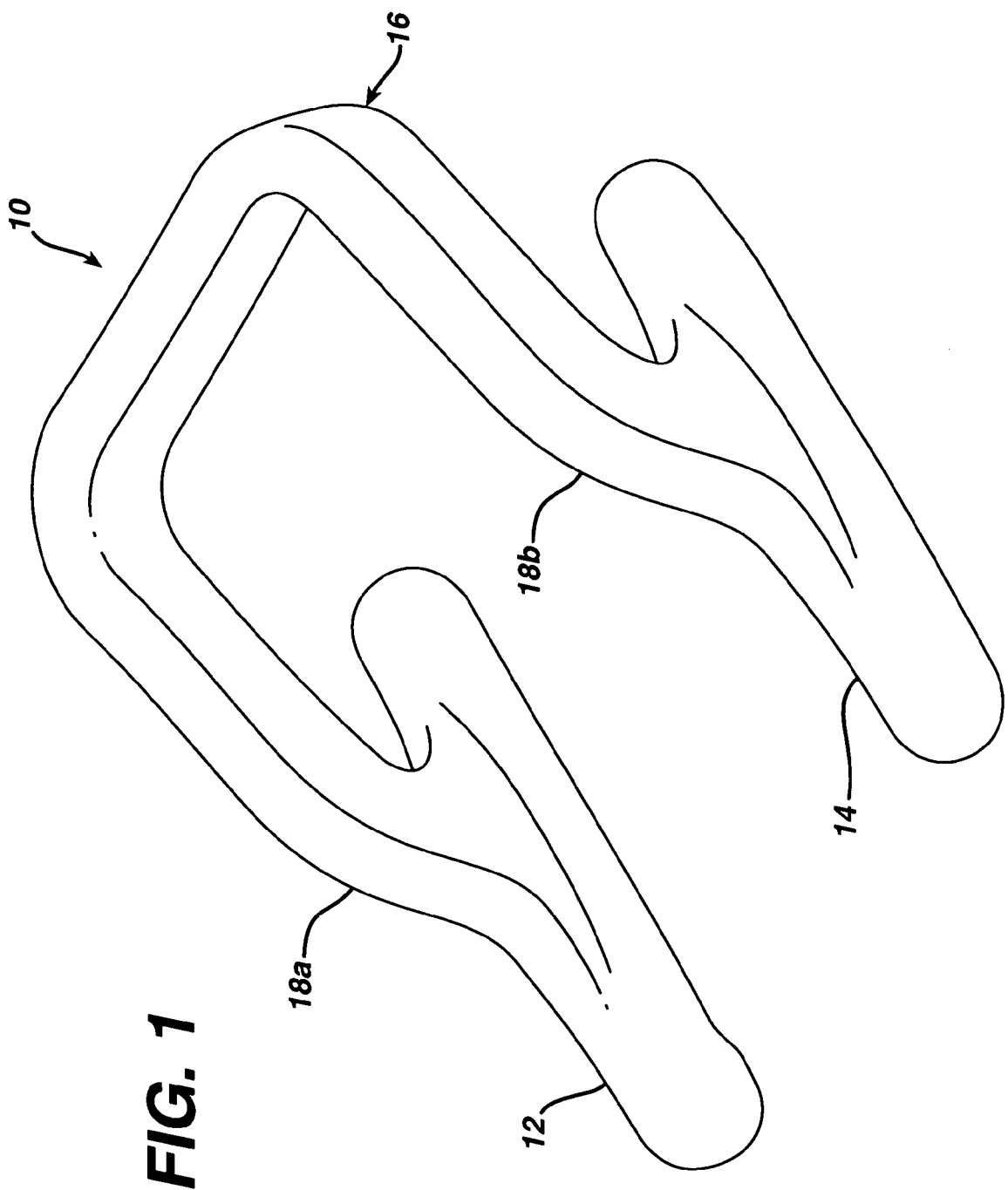
FIG. 1 illustrates one embodiment of a surgical fastener that can be used with the cartridge of the present invention.
Figure 2:
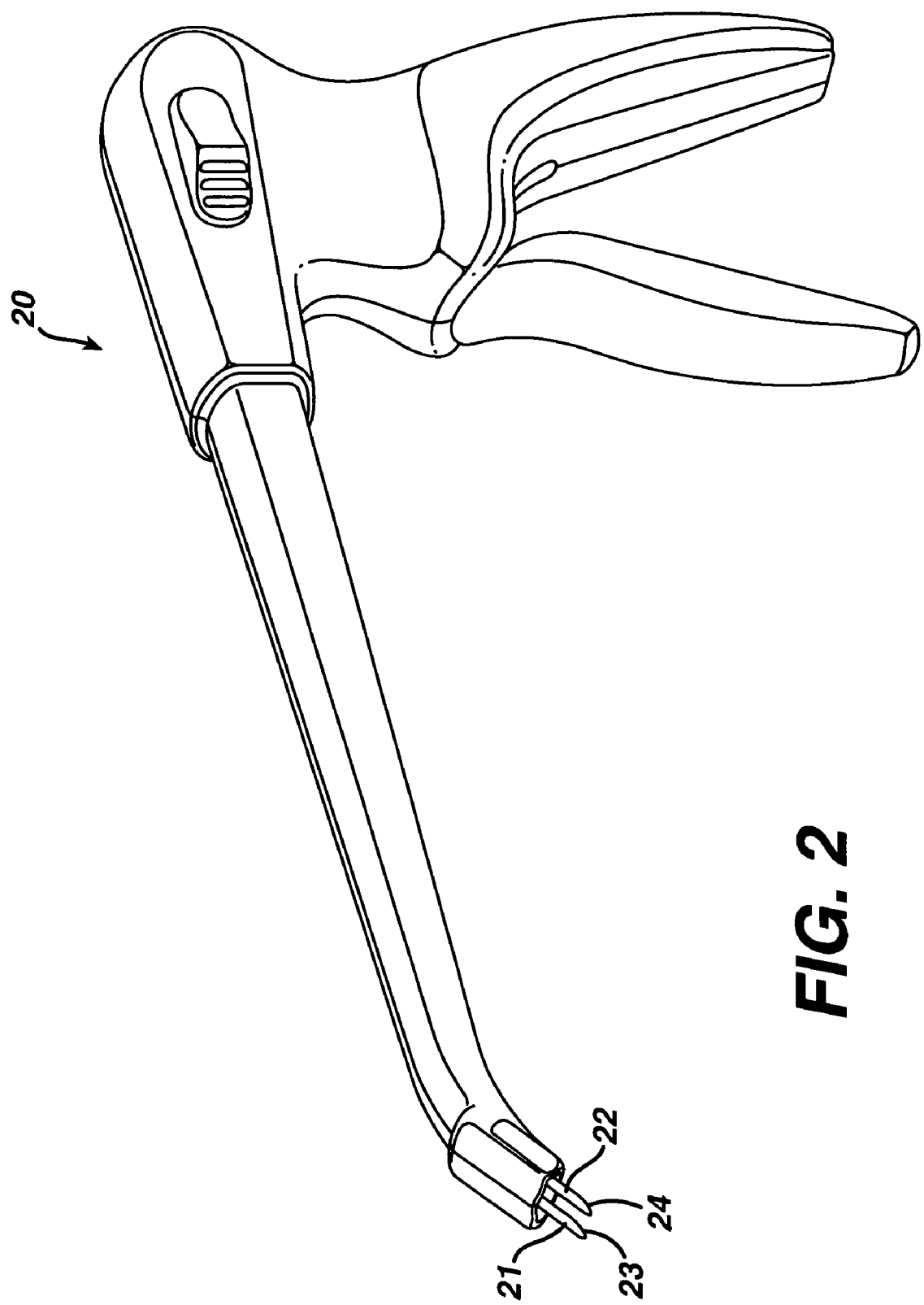
FIG. 2 illustrates one embodiment of a surgical applicator that can be used in conjunction with the present invention.

Referring now generally to FIGS. 3-10, the present invention provides a surgical fastener holding system 40 including a cartridge 41 and one or more shuttles 42 that are removably received within channels 43 in the cartridge. The surgical fastener 10 is pre-loaded in the shuttle 42 (see FIGS. 9a-9c), and the shuttle inserted into the cartridge channel such that the distal end of the surgical applicator can be inserted into a channel 43 to transfer the fastener from the shuttle to the applicator to thereby load the fastener into the applicator (see FIGS. 5-8).

Figure 9A:
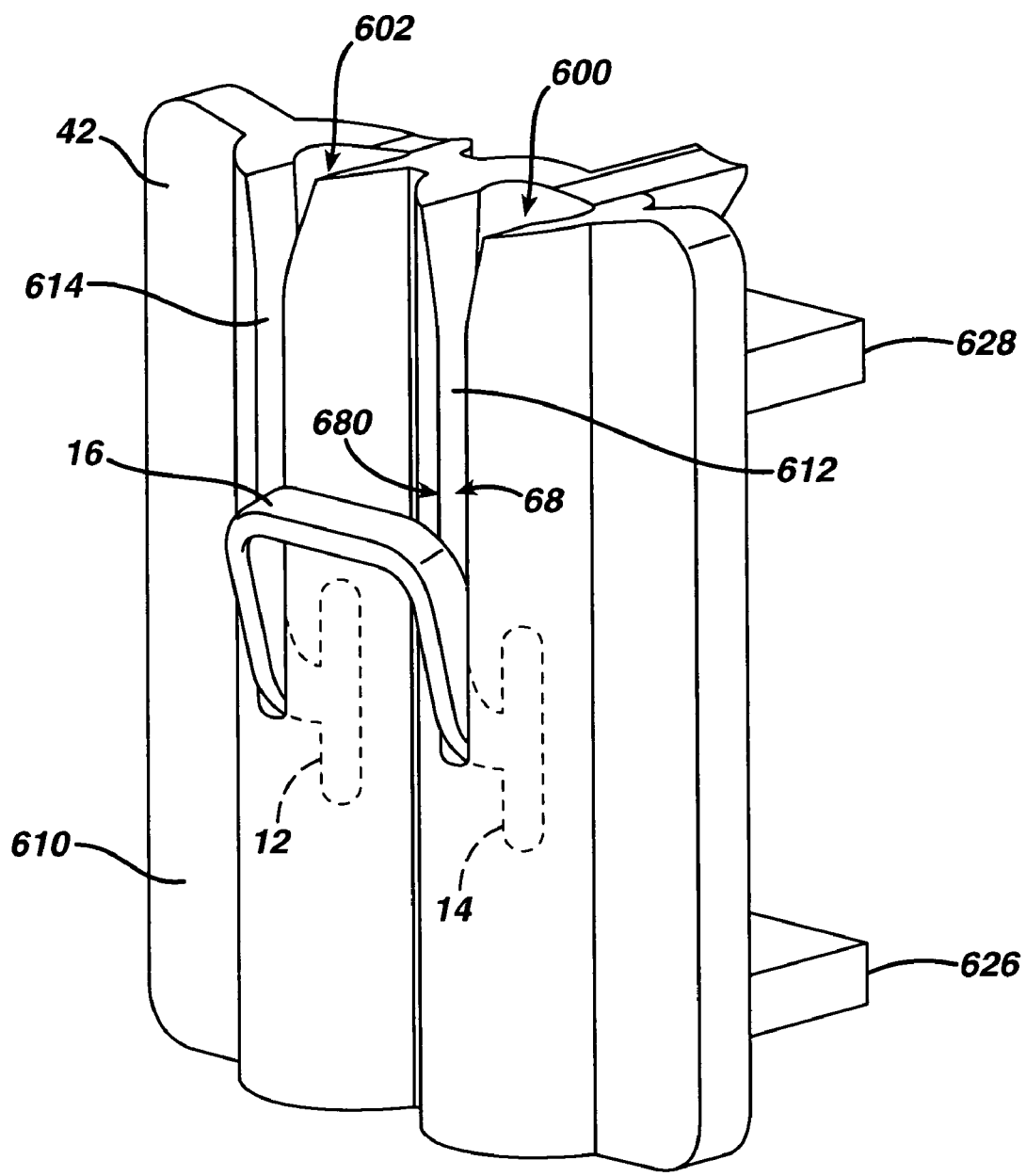
FIGS. 9a-9c are various views of a fastener loaded within a shuttle.

Referring again to FIGS. 9a-9c, shuttle 42 preferably includes first and second channels 600, 602 therein extending inward from openings 604, 606 at the proximal end 608 of the shuttle. A top side 610 of the shuttle also includes grooves 612, 614 that form an opening into the channels 600, 602 respectively along a portion of the length L of the shuttle. These grooves are preferably flared at the proximal end 616, 618 to provide a wider mouth of the grooves. As illustrated, the first and second channels 600, 602 and first and second grooves 612, 614 are dimensioned relative to the first and second anchors 12, 14 so that the first and second anchors can be slidably received within the channels, but not removed from the channels via the grooves. The connecting portion 16 of the fastener, however, extends upwardly out of the grooves as shown in FIG. 9a. The fastener is limited in how far it can be inserted into the shuttle by the connecting portion 16, which abuts the distal end 618, 620 of the grooves. The wider mouth at the proximal end of the grooves facilitates insertion of the first and second anchors into the first and second channels respectively. The shuttle channels and/or grooves may further include some type of projection or the like that helps to secure the fastener within the shuttle. For example, the grooves 612, 614 may include one or more projections 680 extending into the groove. As the fastener is inserted, it is forced over the projections. The projections subsequently help prevent the fastener from inadvertently separating from the shuttle. Alternatively, the channels 600, 602 themselves may include one or more projections or ribs extending therein that create a tighter fit between the fastener anchors and the shuttle.

The shuttle preferably includes first and second side extensions 622, 624 that mate with corresponding grooves 504 on the sides of channel 43 in the cartridge as will be described in greater detail below, and one or more base extensions 626, 628 that are dimensioned to provide a snug fit for the shuttle within the cartridge, and also provide stability to the shuttle when so inserted. The shuttle also preferably includes first and second recesses 630, 632 on its bottom side 634 (see FIG. 7) for mating with one or more projections in the cartridge as will also be described further below.

Figure 6:
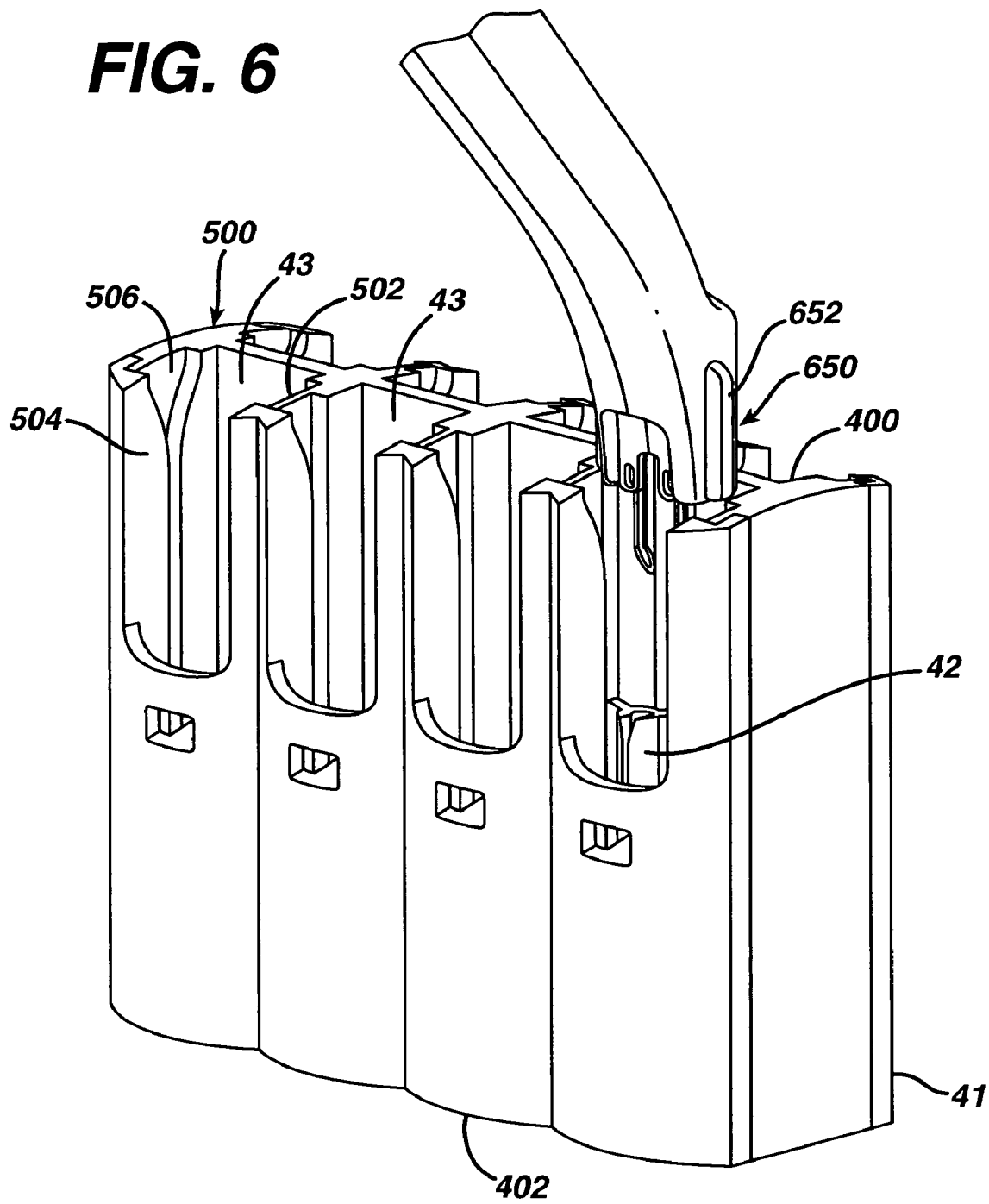
FIG. 6 is a perspective view of FIG. 5.

Referring now to FIG. 6, the cartridge 41 has a proximal end 400 and a distal end 402, and preferably includes a plurality of channels 43 therein, each one of which is capable of removably receiving the shuttle (and fastener) described above. A groove 504 is present on first and second sides 500, 502 of each channel. This groove is dimensioned to receive therein the first and second side extensions 622, 624 of the shuttle in a manner such that the first and second side extensions may slide along the grooves, but so that there is otherwise very little movement of the shuttle relative to the cartridge. Preferably, the grooves 504 each have a flared proximal end 506 to facilitate loading of the shuttle into the cartridge.

Figure 5:
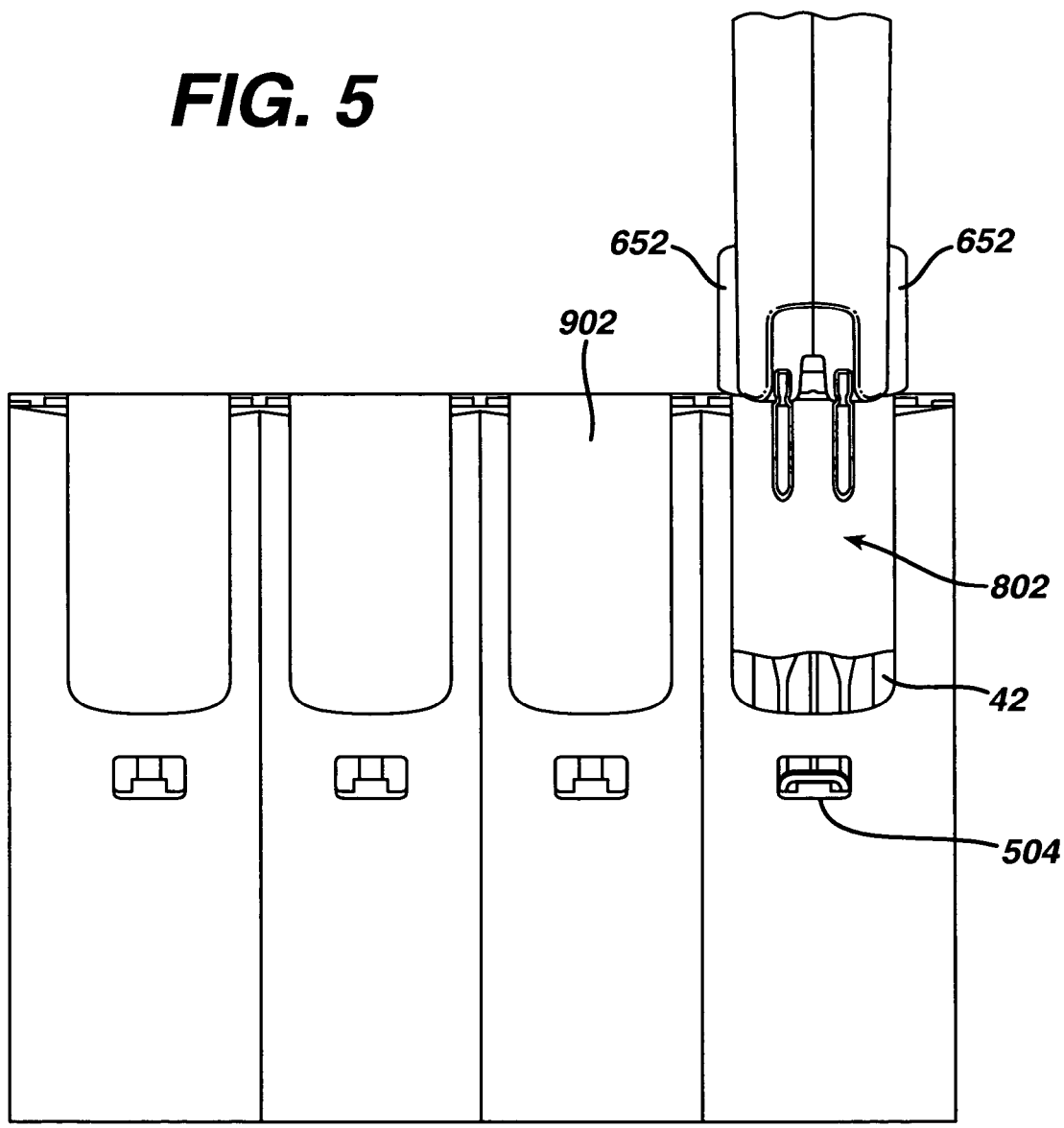
FIG. 5 is a front view of a surgical fastener holding system according to the present invention.
Figure 7:
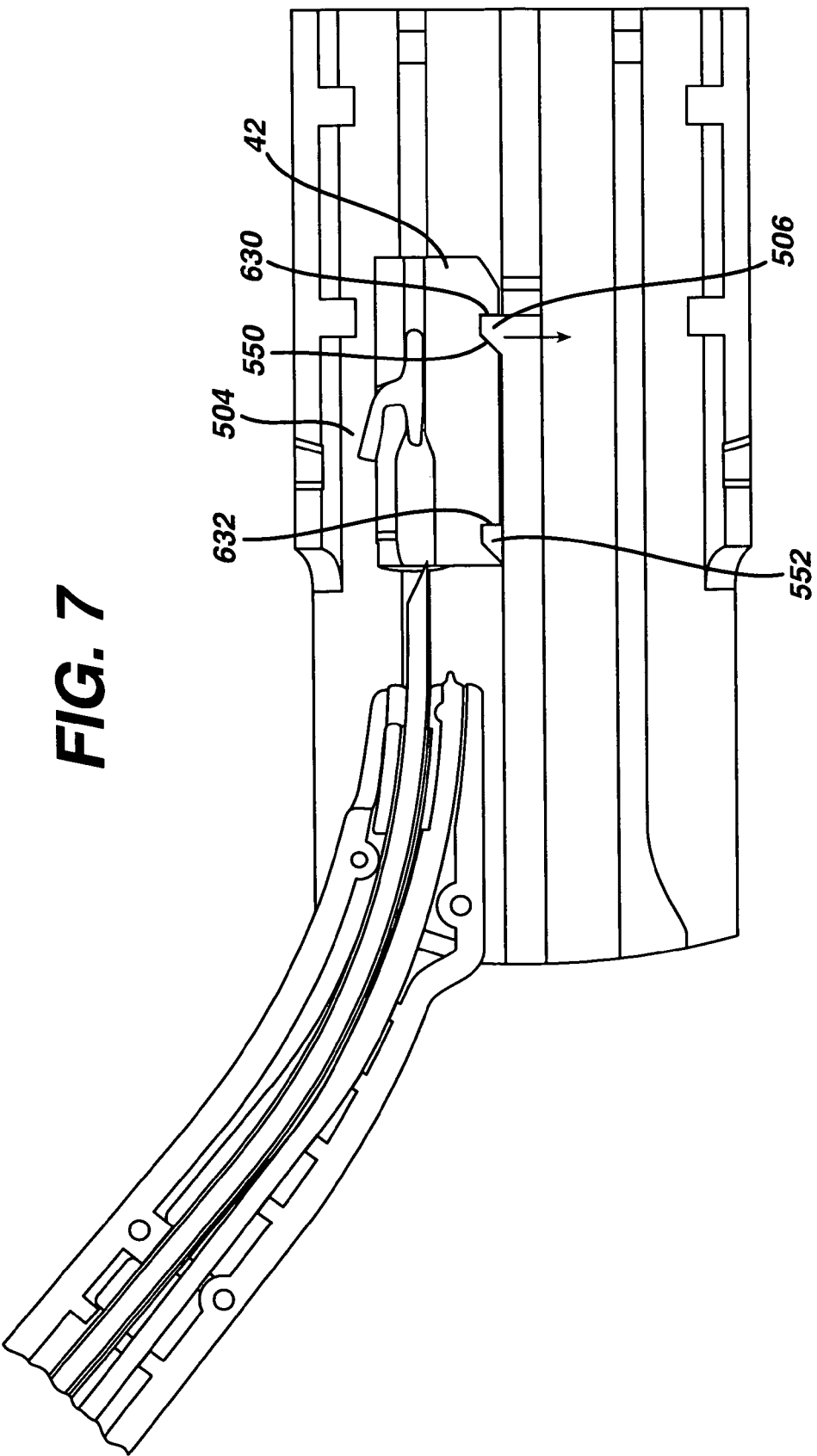

FIG. 5 illustrates each channel 43 having a large opening 802 to the exterior of the cartridge that facilitates positioning of the applicator relative to the shuttle to enable loading of the fastener into the applicator, and also to assist the user in seeing that the applicator is being properly loaded. As is best seen in FIGS. 7 and 8, the upper and lower surfaces of each channel also have first and second projections 504, 506 extending into the channel. These projections are designed to interact with the shuttle in the specific manner described below to facilitate loading of the fastener into the applicator.

Figure 9B:
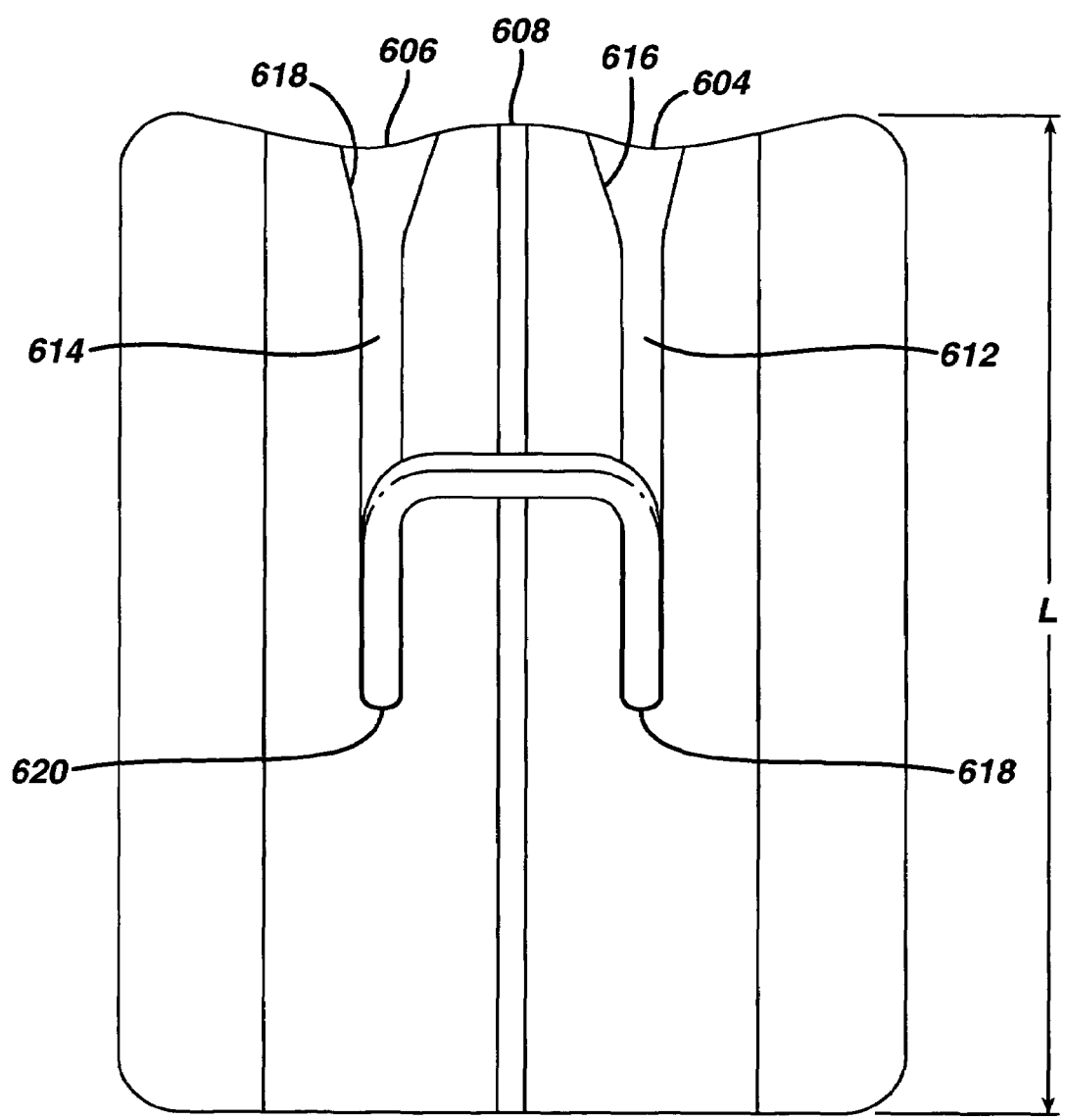
Figure 9C:
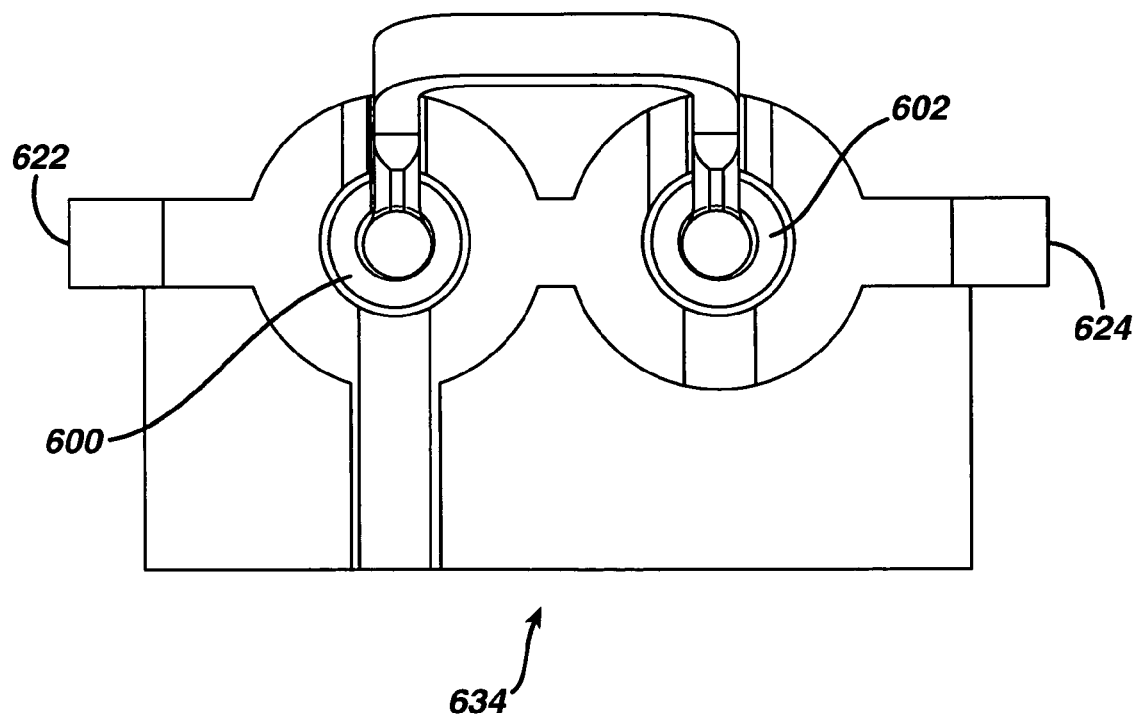

As indicated, the fastener is preloaded into the shuttle in the manner shown in FIGS. 9a-9c. The shuttle is then inserted into the channel 43 of the cartridge 41 by aligning the first and second side extensions 622, 624 of the shuttle with the proximal ends of the channels 504 of the cartridge channels 43 respectively, and sliding the shuttle into the channel. The shuttle is pushed into the channel until the connector portion 16 of the fastener abuts the first projection 504 of the cartridge as shown in FIG. 7, preventing further rearward movement of the fastener within the channel. Preferably, at this point the first recess 630 in the shuttle also engages the second projection 506, preventing further rearward motion of the shuttle. The distal end of the applicator is then inserted into the channel 43 in the manner illustrated in FIG. 7. Preferably, the configuration of the distal end 650 of the applicator facilitates alignment of the needle elements 21, 22 with the first and second anchors 12, 14 respectively. For example, the distal end of the applicator may include first and second flared elements 652 on each side of the applicator that mate with grooves 504.

The proximal ends 616, 618 of the shuttle channels 612, 614 are dimensioned relative to the needles of the applicator so that the ends of the needles can be received therein. Further, the channels 600, 602 are preferably tapered from the proximal end to the distal end so that toward the distal end the channel is just large enough to hold the anchor of the fastener, but not large enough to receive the needles. With the needles aligned with the channels and anchors therein, the distal end of the applicator is pushed forward as shown in FIG. 8. The projection 506 holding the shuttle in position is preferably a tab-like element having an inclined leading edge 550, and preferably is movably mounted to the cartridge. When the force exerted by the applicator on the shuttle exceeds a predetermined force, the second projection moves in the direction of the arrow shown in FIG. 7 until the shuttle is able to pass over the second projection and continue moving toward the distal end of the cartridge. The fastener, however, is still held in place by the first projection 504, so that as the shuttle moves rearward, the anchors of the faster are forcibly ejected from the shuttle and inserted into the channels in the needles of the applicator, thereby fully loading the fastener into the applicator. As the shuttle is moved rearward, the second shuttle recess 632 may eventually engage the second projection, helping to prevent further rearward movement of the shuttle. In addition, the cartridge may also include another projection, stop or the like (not shown) toward the distal end of the channel that will entirely prevent the shuttle from exiting the rear of the cartridge.

In one embodiment of the applicator, the applicator includes a retractable protective shield around the needle elements. This protective shield in its extended position substantially covers the needles to prevent accidental injury from the needles. In its retracted position, however, the needles are fully exposed. When the distal end of the applicator is first inserted into the channel 43 of the cartridge 41, the shield is in the expanded position and will abut the shuttle. When force is applied to the applicator to load the fastener, however, the force required to retract the shield is less than that required to push the shuttle over the second projection 506 as described above. Thus, application of force to the applicator will first cause the shield to retract, and once the needles are exposed will cause the shuttle to move rearward thereby loading the fastener.

Figure 3:
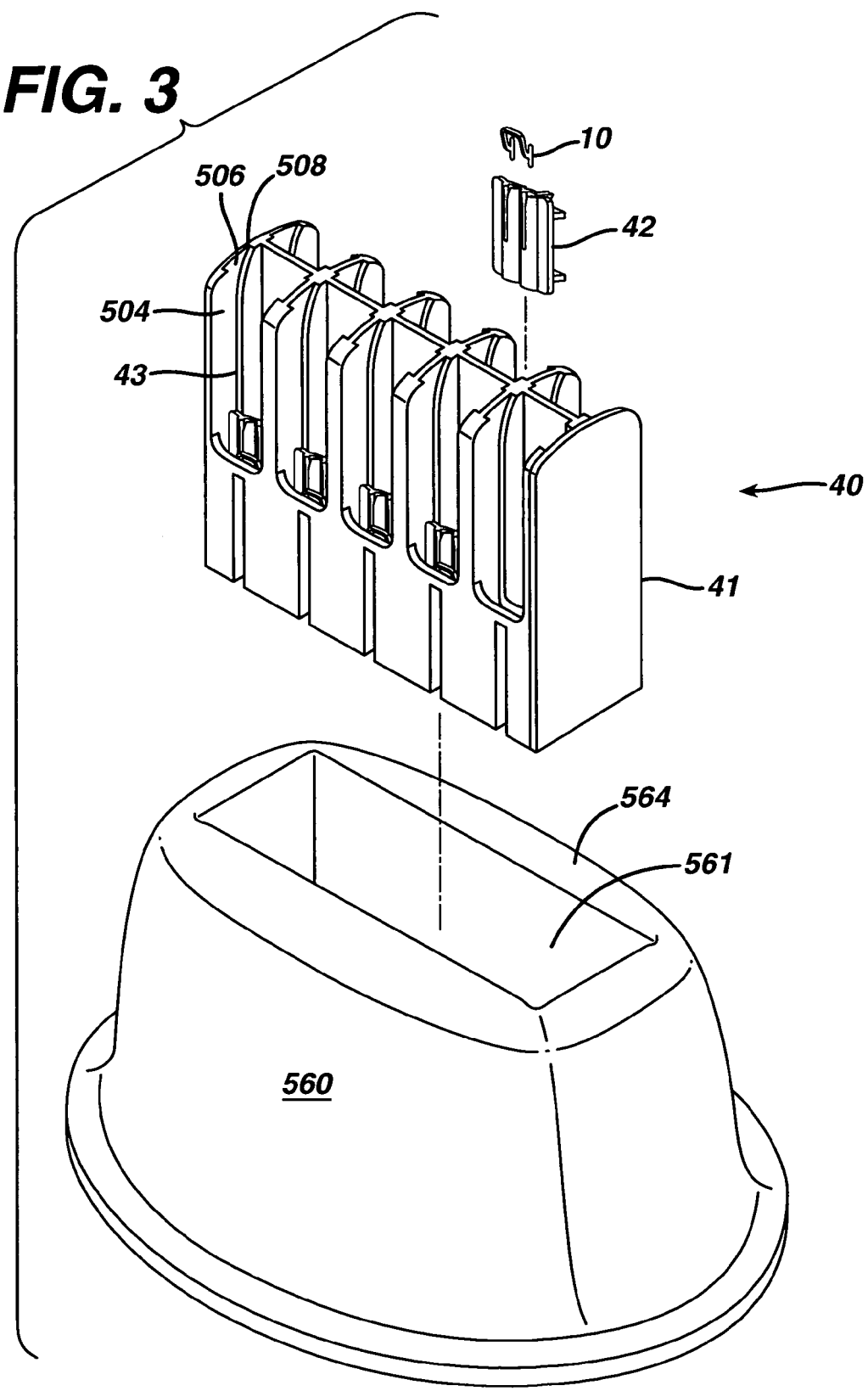
FIG. 3 is an exploded view of a surgical fastener holding system of the present invention.
Figure 4:
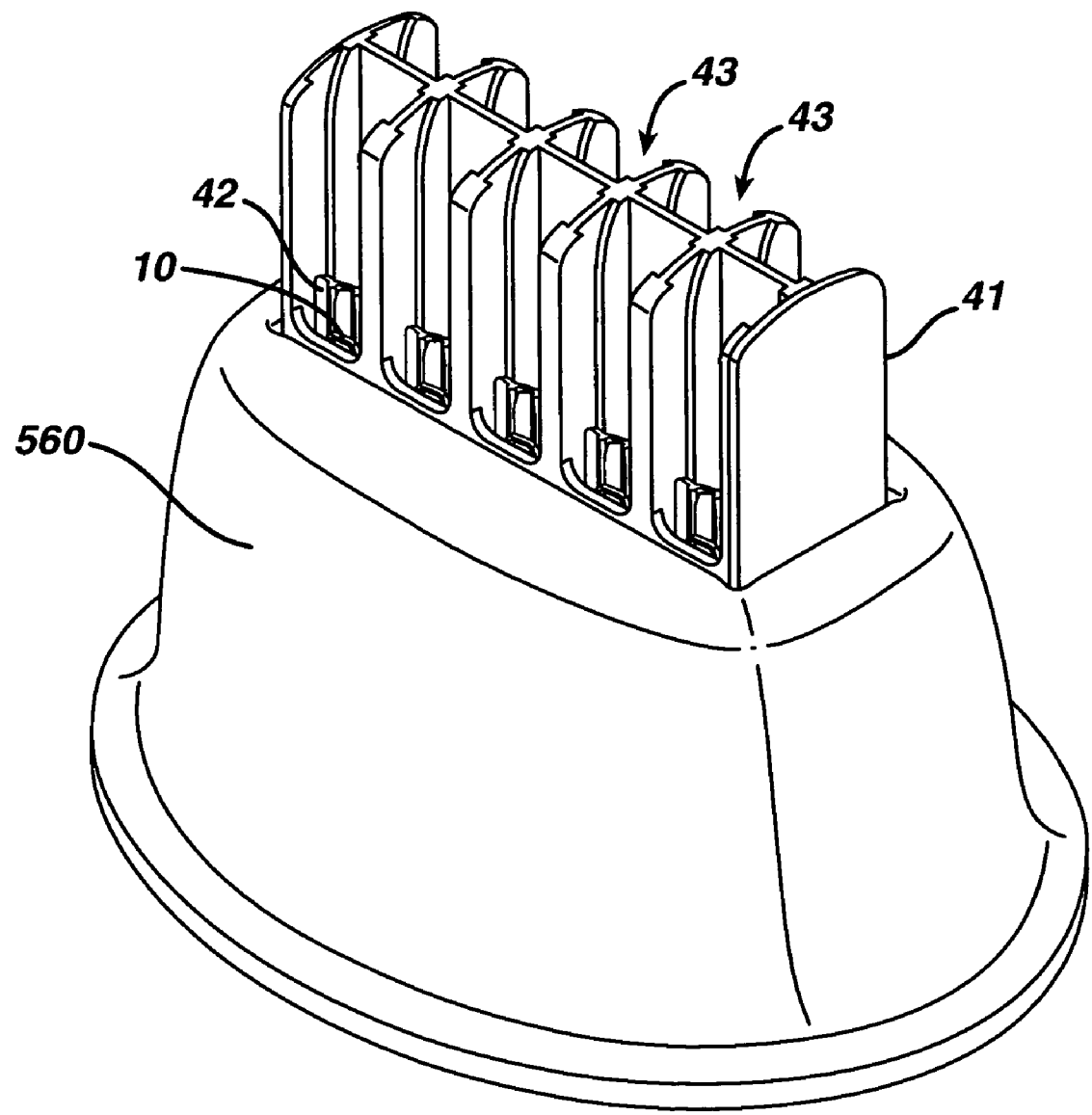
FIG. 4 illustrates the components of FIG. 3 as assembled.
Figure 11:
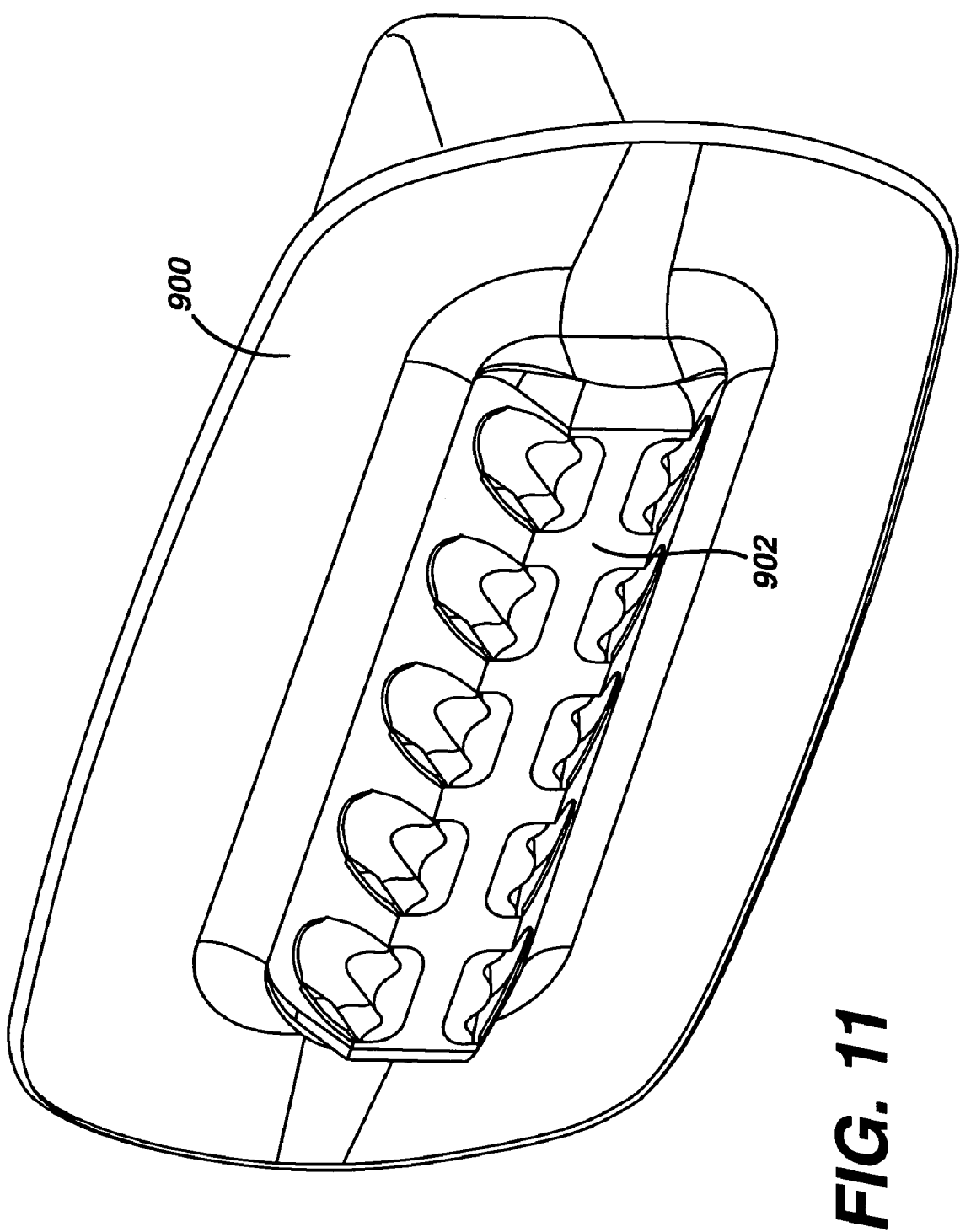
FIG. 11 illustrates an alternate embodiment of a cartridge holder.

The cartridge system may further include a holder such as that shown in FIGS. 3 and 4. The holder 560 has a base end 562 and a top end 564, and a recess 561 therein dimensioned to receive the distal end 402 of the cartridge. The holder is designed to hold the cartridge in place and provide a backstop against which the cartridge can be pushed when loading the fastener into the applicator. The holder may additionally be designed or shaped to assist in gripping the holder while loading the applicator. Another embodiments of a holder is shown in FIG. 11, which includes a flange or the like 900 that partly or fully extends around the periphery of the holder towards its top end 902. This flange allows the user to grip the cartridge at a location distal of the flange, and provides protection for the user's hand as the applicator is being inserted into the cartridge to load the fastener.

Figure 10:
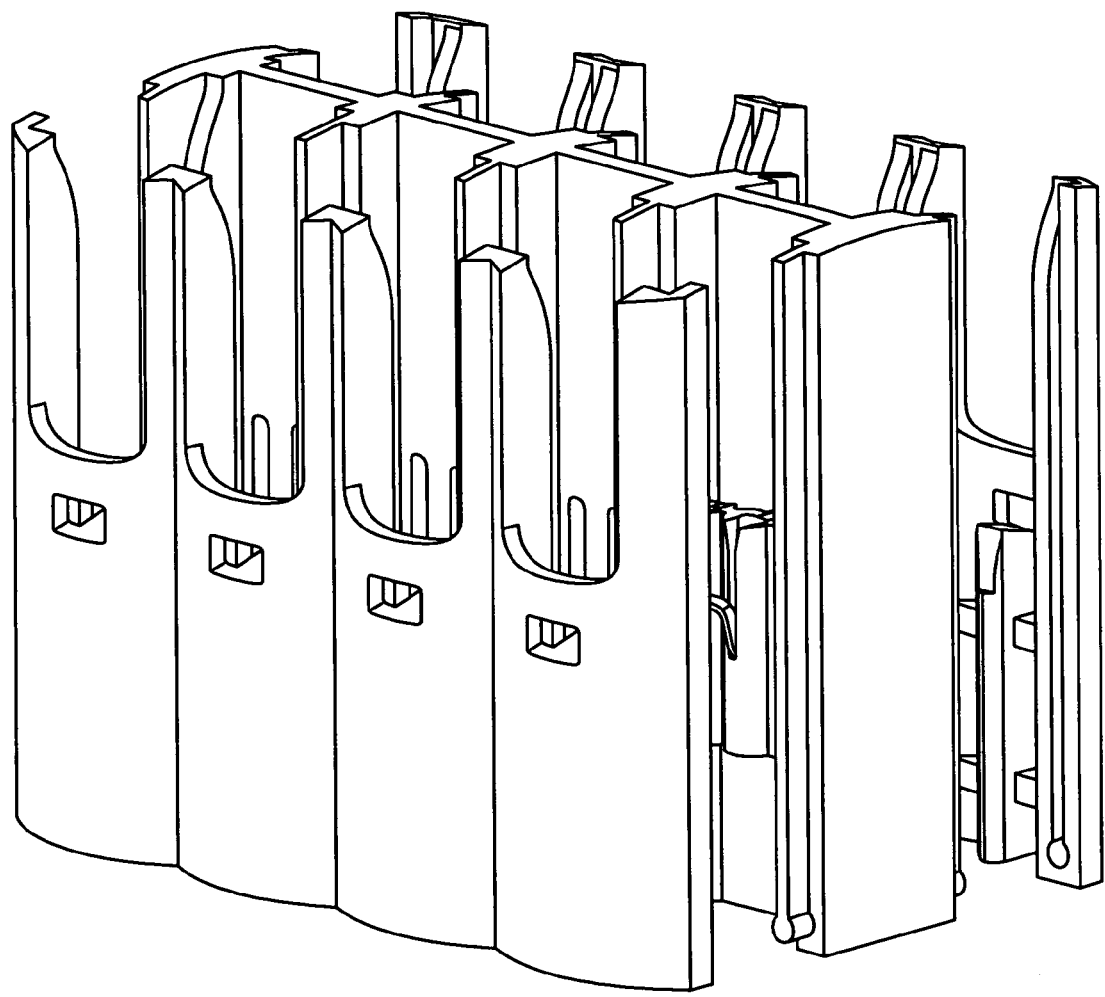
FIG. 10 is an exploded view of one embodiment of a cartridge.

The cartridge may be constructed from a single piece, or may be molded or constructed from three separate pieces as shown in FIG. 10 and snap fit together. A preferred material for the cartridge is a substantially transparent or translucent plastic such as polycarbonate, but various other materials such as nylon are suitable as well. The transparency or translucency assists the user in seeing whether the fastener is properly positioned within the shuttle and cartridge, and is properly being loaded into the applicator.

Although exemplary embodiments and methods for use have been described in detail above, those skilled in the art will understand that many variations are possible without departing from the spirit and scope of the invention, which is limited only by the appended claims.

What is claimed is:

1. A surgical fastener holding system comprising:
   at least a first surgical fastener having a first anchor, a second anchor and a connector extending therebetween upwardly from the first and second anchors;
   a shuttle having first and second channels dimensioned to slidably receive therein the first and second anchors of the surgical fastener, the shuttle further having first and second grooves respectively forming openings into the channels along a portion of a length of the channels, wherein when the first and second anchors are received within the first and second channels, the connector of the surgical fastener extends out of the shuttle through the first and second grooves;
   a cartridge having at least a first channel dimensioned to slidably receive the shuttle therein, and having a first projection extending into the first channel of the cartridge, wherein when the shuttle and loaded fastener are received within the first channel of the cartridge, the connector of the surgical fastener abuts the first projection to thereby limit movement of the fastener toward a distal end of the cartridge.

2. The system according to claim 1, wherein the cartridge has a second projection extending into the cartridge channel, wherein the second projection engages a first recess in the shuttle to prevent further movement of the shuttle toward the distal end of the cartridge absent application of a predetermined amount of force against the shuttle.

3. The system according to claim 2, wherein the second projection is a tab element having an inclined edge and movably mounted to the cartridge, wherein application of said predetermined force to the shuttle causes the second projection to move relative to the cartridge to enable the shuttle to move past the second projection.

4. The system according to claim 2, wherein application of said predetermined force to said shuttle enables the shuttle to move past the second projection toward the distal end of the cartridge, but wherein the first projection still prevents movement of the fastener, thereby causing the first and second fastener anchors to be ejected from the first and second shuttle channels.

5. The system according to claim 4, wherein the cartridge channel is dimensioned to receive therein a distal end of an applicator having first and second hollow needles projecting outwardly therefrom that align with the first and second shuttle channels, wherein as the first and second anchors are ejected from the first and second shuttle channels, they are received within the hollow needles.

6. The system according to claim 1, wherein the cartridge channel is open to an exterior of the cartridge along a portion of the cartridge channel.

7. The system according to claim 1, wherein the cartridge further comprises a plurality of channels for removably receiving a plurality of shuttles.

8. The system according to claim 1, wherein a proximal end of the first and second shuttle channels are flared.

9. The system according to claim 1, wherein the cartridge further comprises first and second recesses adjacent first and second sides of the cartridge channel respectively, and wherein the shuttle further comprises first and second side extensions dimensioned to be received within the first and second recesses when the shuttle is inserted into the cartridge channel.

10. The system according to claim 9, wherein a proximal end of the first and second recesses is flared.

11. The system according to claim 1, further comprising a cartridge holder having a base side and a top side, the top side having a recess therein dimensioned to receive the distal end of the cartridge to thereby hold the cartridge in position relative to a surface on which the cartridge holder is placed.

12. The system according to claim 11, wherein the cartridge holder further comprises a shield element extending outwardly from the cartridge holder toward the top side of the cartridge holder, the shield element extending around at least a portion of a periphery of the cartridge holder.

13. A surgical fastener holding system comprising:
a surgical fastener having first and second anchors and a connector extending therebetween upwardly from the first and second anchors;
a shuttle having first and second channels dimensioned to slidably receive therein the first and second anchors of the surgical fastener, the shuttle further having first and second grooves forming openings into the first and second channels respectively along a portion of a length of the channels, wherein when the first and second anchors are received within the first and second channels, the connector of the surgical fastener extends out of the shuttle through the first and second grooves;
a cartridge having a proximal end, a distal end, and a channel therein extending inwardly from the proximal end, the cartridge channel being dimensioned to slidably receive therein the shuttle, and having first and second projections extending into said channel,
wherein when the shuttle and loaded fastener are received therein, is slidably received within the cartridge channel, the connector of the surgical fastener abuts the first projection to thereby limit further movement of the surgical fastener toward the distal end of the cartridge, and a recess in the shuttle engages the second projection to prevent further movement of the shuttle toward the distal end of the cartridge absent application of a predetermined amount of force against the shuttle.

14. The system according to claim 13, wherein the second projection is a tab element having an inclined edge and movably mounted to the cartridge such that application of said predetermined force to the shuttle causes the second projection to move relative to the cartridge channel to enable the shuttle to move past the second projection.

15. The system according to claim 14, wherein the shuttle includes a second recess therein that engages the second projection after the first shuttle recess has moved distal of the second projection.

16. The system according to claim 13, wherein application of said predetermined force to said shuttle enables the shuttle to move past the second projection toward the distal end of the cartridge, but wherein the first projection still prevents movement of the fastener, thereby causing the first and second fastener anchors to be ejected from the first and second shuttle channels.

17. The system according to claim 16, wherein the cartridge channel is dimensioned to receive therein a distal end of an applicator having first and second hollow needles projecting outwardly therefrom that align with the first and second shuttle channels, wherein as the first and second anchors are ejected from the first and second shuttle channels, they are received within the hollow needles.

18. The system according to claim 13, wherein the cartridge further comprises a plurality of channels for removably receiving a plurality of shuttles.

19. The system according to claim 13, wherein the cartridge further comprises first and second recesses adjacent first and second sides of the cartridge channel respectively, and wherein the shuttle further comprises first and second side extensions dimensioned to be received within the first and second recesses when the shuttle is inserted into the cartridge channel.

20. A method for loading a surgical fastener into an applicator, the method comprising the steps of:
providing a surgical fastener having a first anchor, a second anchor and a connector extending therebetween upwardly from the first and second anchors;
providing a shuttle having first and second channels therein, and first and second grooves respectively forming openings into the channels along a portion of a length of said channels;
inserting the first and second anchors of the surgical fastener into the first and second shuttle channels such that the connector of the surgical fastener extends out of the shuttle through the first and second grooves;
providing a cartridge having at least a first channel therein and a first projection extending into the first channel;
inserting the shuttle and inserted fastener into the cartridge first channel such that the connector of the surgical fastener abuts the first projection to thereby limit further movement of the fastener toward a distal end of the cartridge;

inserting an applicator having first and second hollow needles extending from a proximal end thereof into the cartridge channel such that the first and second hollow needles are aligned with the first and second shuttle channels; and inserting the applicator further into the cartridge channel to push the shuttle further toward a distal end of the cartridge such that the first and second anchors of the surgical fastener are ejected from the first and second shuttle channels into the first and second hollow needles of the applicator.

* * * * *